(12) United States Patent
Anderson

(10) Patent No.: US 10,524,803 B1
(45) Date of Patent: *Jan. 7, 2020

(54) SURGICAL SAW BLADE AND METHOD FOR WEDGE OSTEOTOMIES

(71) Applicant: Keith Richard Anderson, Blaine, MN (US)

(72) Inventor: Keith Richard Anderson, Blaine, MN (US)

(73) Assignee: Cortical Edge Orthopedics, LLC, Otsego, MN (US)

( * ) Notice: Subject to any disclaimer, the term of this patent is extended or adjusted under 35 U.S.C. 154(b) by 339 days.

This patent is subject to a terminal disclaimer.

(21) Appl. No.: 14/605,634

(22) Filed: Jan. 26, 2015

Related U.S. Application Data

(63) Continuation of application No. 12/732,398, filed on Mar. 26, 2010, now Pat. No. 8,939,981.

(60) Provisional application No. 61/164,594, filed on Mar. 30, 2009.

(51) Int. Cl.
*A61B 17/14* (2006.01)

(52) U.S. Cl.
CPC ............ *A61B 17/141* (2013.01); *A61B 17/14* (2013.01)

(58) Field of Classification Search
CPC ..... A61B 17/14; A61B 17/141; A61B 17/148; A61B 17/1659
USPC ......................................... 606/79, 82, 84, 85
See application file for complete search history.

(56) References Cited

U.S. PATENT DOCUMENTS

| | | | |
|---|---|---|---|
| 254,733 A | 3/1882 | Valentine | |
| 349,119 A * | 9/1886 | Phillips | B25D 3/00 30/168 |
| 435,538 A | 9/1890 | Fletcher | |
| 1,507,264 A | 9/1924 | Stevenson | |
| D282,205 S | 1/1986 | Davison et al. | |
| 4,625,725 A | 12/1986 | Davison et al. | |
| 5,087,261 A * | 2/1992 | Ryd | B23D 49/003 30/123.3 |
| 5,342,365 A | 8/1994 | Waldman | |
| 5,441,501 A | 8/1995 | Kenyon | |
| 5,569,257 A | 10/1996 | Arnegger et al. | |
| 5,620,448 A | 4/1997 | Puddu | |
| 5,690,316 A | 11/1997 | Madjarac | |
| 5,749,875 A | 5/1998 | Puddu | |
| 6,120,508 A | 9/2000 | Grunig et al. | |
| D612,050 S | 3/2010 | Baynham | |
| 2005/0113840 A1 | 5/2005 | Metzger et al. | |
| 2007/0233131 A1* | 10/2007 | Song | A61B 17/1671 606/79 |

(Continued)

OTHER PUBLICATIONS

Web pages displaying surgical saw blade images, available at http://vilex.com/vilex-surgical-products/power-equipment-and-accessories/hand-pieces-and-accessories (last visited Aug. 19, 2014).

*Primary Examiner* — Si Ming Ku
(74) *Attorney, Agent, or Firm* — Faegre Baker Daniels LLP

(57) ABSTRACT

A surgical blade and method for performing a one-pass wedge osteotomy. The blade includes a body portion, having a cutting tip on a first end for initially cutting into the bone; a cutting slope comprising multiple rows of cutting teeth at multiple planes to resect bone as it enters, leaving a wedge osteotomy; a shaft of a predetermined length and width for supporting the cutting slope; and a saw attachment base on a second end of the blade for engaging a base of a saw to cause the blade to oscillate and perform the wedge osteotomy.

24 Claims, 3 Drawing Sheets

(56) References Cited

U.S. PATENT DOCUMENTS

2009/0312762 A1    12/2009  Boykin

\* cited by examiner

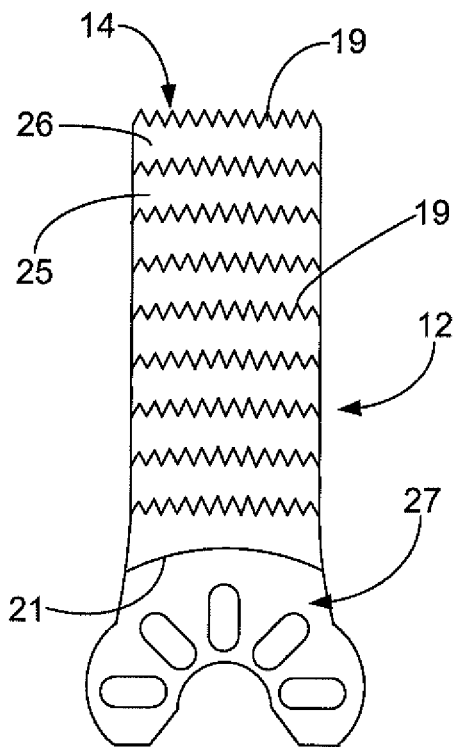
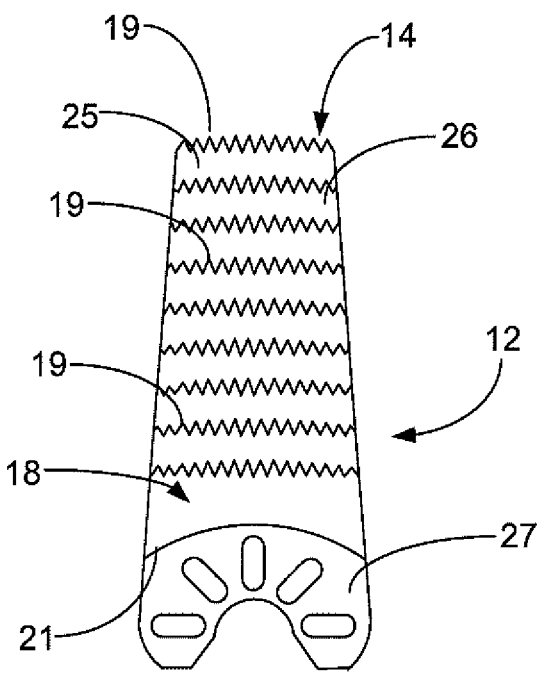
FIG. 4
FIG. 7
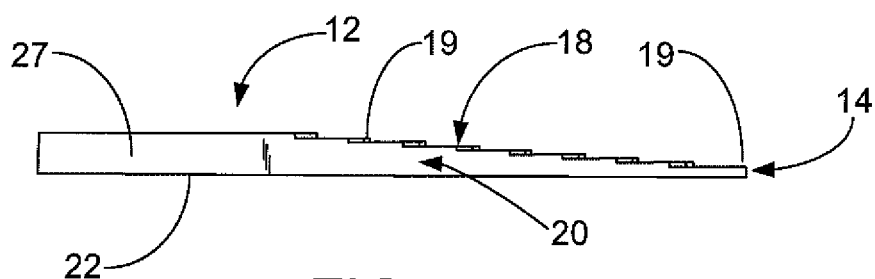
FIG. 5
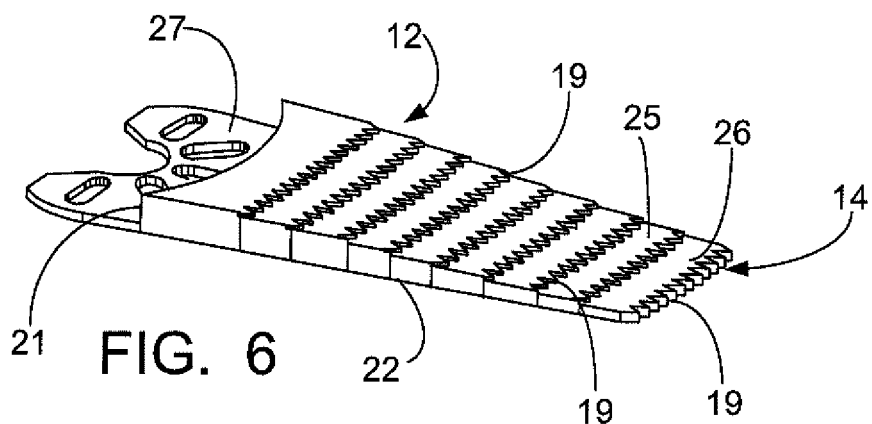
FIG. 6

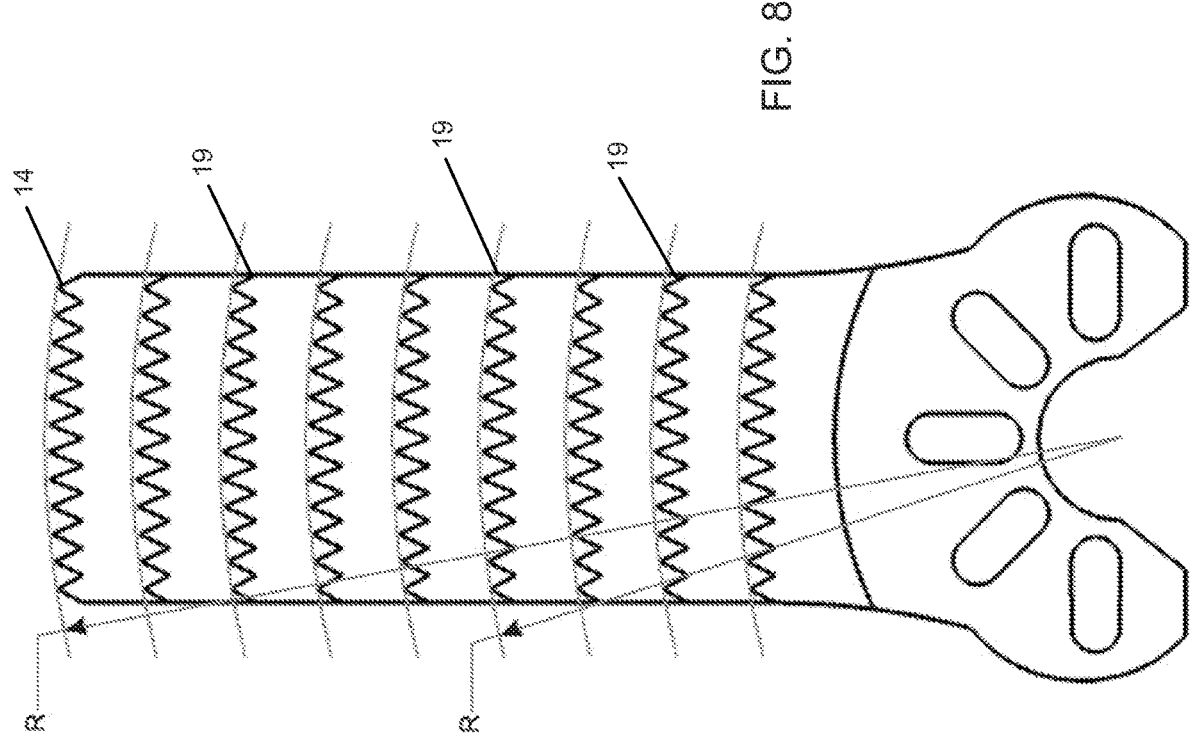

SURGICAL SAW BLADE AND METHOD FOR WEDGE OSTEOTOMIES

CROSS-REFERENCE TO RELATED APPLICATIONS

This is a continuation of U.S. patent application Ser. No. 12/732,398, filed Mar. 26, 2010 (issued as U.S. Pat. No. 8,939,981 on Jan. 27, 2015), which claims the benefit of U.S. Provisional Patent Application Ser. No. 61/164,594, filed Mar. 30, 2009, each of which is hereby incorporated herein by reference.

Priority of U.S. patent application Ser. No. 12/732,398, filed Mar. 26, 2010 and U.S. Provisional Patent Application Ser. No. 61/164,594, filed Mar. 30, 2009, which are incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention generally relates to surgical devices. More particularly, the present invention relates to a surgical saw blade for wedge osteotomies.

2. General Background of the Invention

Current surgical saw blades make straight or crescentic shaped osteotomies. This causes the user to make multiple osteotomies to resect a wedge of bone. Creation of multiple osteotomies is time consuming, and can create inconsistent wedge sizes and planar inaccuracies.

As can be seen, there is a need for a surgical saw blade for precise, reproducible, and predictable wedge osteotomies.

BRIEF SUMMARY OF THE INVENTION

The apparatus of the present invention solves the problem in a simple and straightforward manner. What is provided is a surgical blade for use with a saw, the bland which. Includes a cutting tip, having a plurality of cutting teeth; a shaft having a cutting slope, with the plurality of teeth positioned along multiple planes on the cutting slope; a neck portion; and a saw base; wherein the saw causes the blade to oscillate as it undergoes the cutting procedure.

These and other features, aspects and advantages of the present invention will become better understood with reference to the following drawings, description and claims.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 4 illustrates a top view of a second embodiment of the invention;

FIG. 5 illustrates a side view of a second embodiment of the invention;

FIG. 6 illustrates an overall view of a third embodiment of the invention;

FIG. 7 illustrates a top view of a third embodiment of the invention; and

FIG. 8 illustrates a top view of an embodiment of the invention and shows the rows of cutting teeth and cutting tip having a radius.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

An embodiment of the present invention adds a slope on one side of the blade from the distal tip to the proximal shaft with teeth to allow for a precise predetermined wedge of bone to be resected with performing only one osteotomy. The present invention relates to a surgical saw blade for precise, reproducible, and predictable wedge osteotomies.

Embodiments of the present invention include a surgical saw blade for creating precise wedge osteotomies that are reproducible and predictable, to be used to correct angular deformities in bones and joints. An embodiment of the invention, which may be called a "wedge osteotomy blade," creates a precise predetermined wedge cut in bone with one pass. This can eliminate the need for two passes with a standard bone saw blade, as well as eliminate planar inconsistencies associated with multiple passes. The osteotomy is reproducible and predictable.

Figure 1:
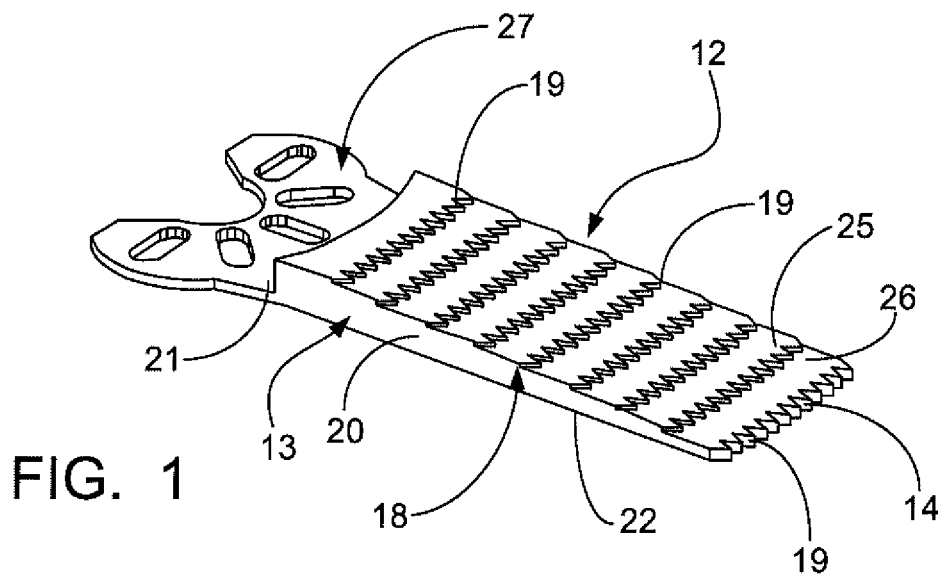
FIG. 1 illustrates an overall view of a first embodiment of the invention.
Figure 2:
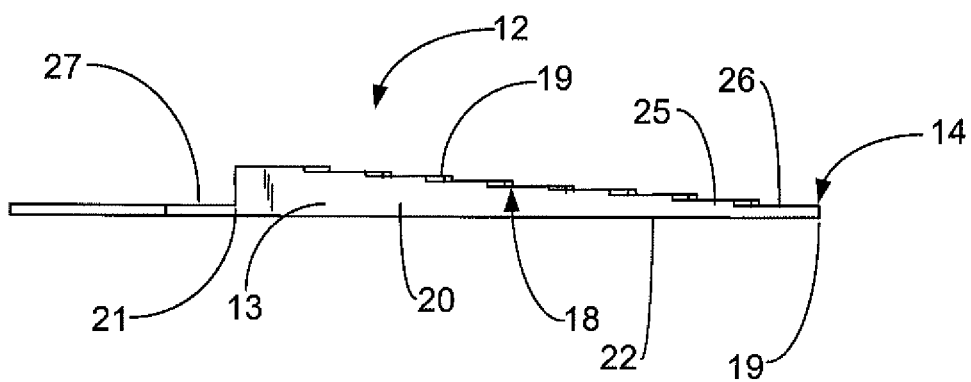
FIG. 2 illustrates a side view of a first embodiment of the invention.
Figure 3:
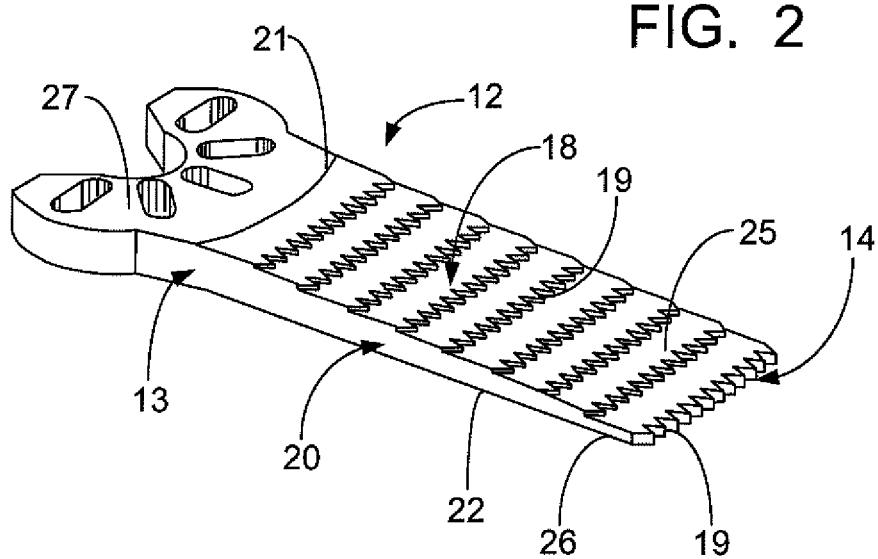
FIG. 3 illustrates an overall view of a second embodiment of the invention.

FIGS. 1 through 8 illustrate the preferred embodiments of the device of the present invention. Broadly, each embodiment of the present invention, as illustrated in FIGS. 1 through 8, is generally a surgical saw blade 12 for precise, reproducible, and predictable wedge osteotomies. Although each embodiment has slight modifications over other embodiments, it should be known that the principal inventive features as claimed are found in each embodiment as shown in the FIGS. 1 through 8.

In each embodiment, the wedge osteotomy blade 12 is a device designed to create a precise, predetermined wedge osteotomy in bone. The wedge osteotomy blade 12 could be retro-fitted to any surgical saw configuration. The wedge osteotomy blade 12 could be constructed of surgical grade stainless steel or any other material used for cutting bone that can be sterilized.

The blade 12 further comprises a blade body 13 having a cutting tip 14 which is designed with multiple teeth 16 to create a cut in bone when oscillated. This tip 14 preferably has a radius R, and could contain any number of teeth. The radius R is illustrated in FIG. 8. The teeth could be any length or of any design.

There is provided a cutting slope 18 designed on one side 21 of a shaft 20, with the underside 22 being flat. The cutting slope 18 could be any rise over run desired for creating a wedge osteotomy. The slope should be at its highest height near the neck 24 and at its lowest height at the cutting tip 14.

The cutting slope 18 has multiple rows of cutting teeth 19. Each row of teeth 19 is elevated above the run of the distal row of teeth 19. The cutting teeth 19 could be of any design and preferably have the same radius, number of teeth, and same length as the cutting tip 14.

The shaft 20 is designed to be flat on four surfaces and accommodates the cutting slope 18 on the fifth surface 25, and the cutting tip 14 on the sixth surface 26. The shaft 20 could be of any shape, preferably rectangular or trapezoidal. The shaft 20 extends from the neck 21 to the cutting tip 14. The shaft 20 could be any length and width.

The neck 21 is designed to be the transition from the shaft 20 to the saw attachment base 27.

The saw attachment base 27 allows the blade 12 to be attached to a surgical saw (not illustrated).

The invention provides the surgeon a way to make accurate wedge osteotomies with predictability and reproducibility. The wedge osteotomy blade 12 has a cutting tip 14 to start the osteotomy. The cutting slope 18 resects bone as it enters, leaving a wedge osteotomy. The cutting slope 18 has rows of cutting teeth 19 for resection of bone while oscillating. The shaft 20 is of a predetermined length and width and supports the cutting slope 18. The neck 21 is the transition of the shaft 20 into the saw attachment base 27. The saw attachment base 27 can be of any design to fit any number of surgical saw manufacturers.

The wedge osteotomy blade 12 is one component. It can be manufactured from surgical grade stainless steel or any other material used for cutting bone that can be sterilized.

The wedge osteotomy blade 12 works by creating a precise, predetermined, wedge osteotomy in bone. To perform an osteotomy with the wedge osteotomy blade 12, the Surgeon has to first attach the blade 12 to a surgical saw (not illustrated). The surgical saw could be from any manufacturer. The wedge osteotomy blade 12 which is being oscillated by the surgical saw is then introduced into the bone in a straight fashion. The surgeon can dictate whether to make a complete through and through osteotomy, or leave the distal cortex intact as a hinge. After satisfactory wedge resection, saw is disengaged and removed from bone. It leaves a precise, predetermined, wedge osteotomy for the surgeon to correct angular deformities in bones and joints.

To make this invention a detailed drawing, or a computer aided design drawing is needed. With the aforementioned drawings, one could machine a wedge osteotomy blade from surgical grade stainless steel or any other material used for cutting bone that can be sterilized.

Another way to reconfigure the wedge osteotomy blade 12 would be to have the cutting slope 18 on two opposite sides of the shaft 20 to create a two sided cutting surface for a "V" type wedge resection, instead of the "right triangle" shaped wedge.

A person would use the invention in the following way. First the saw attachment base 27 is attached to a surgical saw from any number of manufactures. The next step would be to turn the surgical saw on, which in turn would oscillate the wedge osteotomy blade 12. The surgeon then engages the bone with the cutting tip 14 first. As the surgeon advances the blade 12 in a linear fashion through the bone the cutting slope 18 resects a wedge of bone with precision, predictability, and reproducibility.

It should be understood, of course, that the foregoing relates to exemplary embodiments of the invention and that modifications may be made without departing from the spirit and scope of the invention as set forth in the following claims.

The following is a list of parts and materials suitable for use in the present invention.

| PARTS LIST | |
| --- | --- |
| Part Number | Description |
| 12 | wedge osteotomy blade |
| 13 | blade body |
| 14 | cutting tip |
| 18 | cutting slope |
| 19 | cutting teeth |
| 20 | shaft |
| 21 | neck |
| 22 | underside |
| 25 | fifth surface |
| 26 | sixth surface |
| 27 | saw attachment base |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A method for performing a wedge osteotomy comprising:
    providing a surgical saw blade comprising a bottom plane, a cutting point, and a cutting slope, the cutting slope comprising a plurality of offset planes positioned along the cutting slope, the cutting slope defining a second plane that intersects the bottom plane, each of the plurality of offset planes having an upper surface that is parallel to the bottom plane, and the cutting slope further comprising a plurality of rows of teeth, each of the plurality of rows of teeth positioned between the cutting slope and the offset planes;
    attaching the surgical saw blade to a saw;
    selecting a desired area of a bone for resection; and
    initiating a cut in the bone with the cutting point and advancing the surgical saw blade through the bone to create a wedge osteotomy.

2. The method of claim 1 wherein the saw is an oscillating saw or a sagittal saw.

3. The method of claim 1 wherein the cutting point has a radius.

4. The method of claim 3 wherein each of the plurality of rows of teeth comprise a plurality of teeth having cutting tips extending in the direction of the cutting point, the teeth of each row positioned along a radius.

5. The method of claim 1 wherein the surgical saw blade comprises a trapezoidal shape.

6. The method of claim 1 wherein the surgical saw blade comprises a rectangular shape.

7. The method of claim 1 wherein the surgical saw blade is advanced through the bone with one pass of the blade to form a complete wedge osteotomy.

8. The method of claim 1 wherein the surgical saw blade is advanced through the bone leaving a distal cortex of the bone left intact as a hinge.

9. The method of claim 1 wherein the surgical saw blade does not have teeth on four surfaces and accommodates the cutting slope on a fifth surface, and the cutting point on a sixth surface.

10. The method of claim 1, wherein the surgical saw blade comprises a neck portion and a saw attachment base.

11. The method of claim 1, wherein advancing the surgical saw blade through the bone comprises oscillating the surgical saw blade parallel to the bottom plane.

12. The method of claim 1, wherein advancing the surgical saw blade through the bone comprises oscillating the surgical saw blade parallel to the first bottom plane such that the plurality of rows of teeth resects the bone.

13. The method of claim 1, wherein the surgical saw blade further comprises a second cutting slope on an opposite side of the bottom plane from the cutting slope, such that the surgical saw blade is configured to form a "V" shaped wedge osteotomy.

14. A method of performing a one-pass wedge osteotomy comprising:
 a) attaching a surgical saw blade capable of producing a reproducible and predictable wedge osteotomy with one pass of the surgical saw blade to a saw, the surgical saw blade comprising,
  i) a blade body having first and second ends and a bottom with a bottom plane,
  ii) a first plurality of cutting teeth establishing a cutting point on the first end of the blade body for initiating a cut in a bone, and the cutting point having a radius;
  iii) a shaft having a cutting slope defining a second plane that intersects the bottom plane;
  iv) a plurality of offset planes positioned along the cutting slope, each offset plane having an upper surface that is parallel to the bottom plane; and
  v) a plurality of rows of teeth positioned between the upper surface of the offset planes and the cutting slope, each row of teeth having multiple teeth comprising cutting tips extending towards the cutting point and spaced along a radius;
 b) selecting a desired area of the bone for resection; and
 c) advancing the surgical saw blade through the bone, with one pass of the surgical saw blade, and creating a wedge osteotomy.

15. The method of claim 14 wherein the surgical saw blade further comprises a saw attachment point on the second end of the blade body.

16. The method of claim 14 wherein the method includes initiating the cut in the bone with the cutting point of the blade and advancing the blade in a linear or straight fashion through the bone to create the wedge osteotomy.

17. A surgical blade for performing a wedge osteotomy comprising:
 a blade having a bottom plane defining first and second ends, and a cutting slope defining a second plane that intersects the bottom plane;
 the cutting slope of the blade comprising a plurality of offset planes, each of the plurality of offset planes having an upper surface that is parallel to the bottom plane and the plurality of offset planes positioned along the cutting slope, and wherein a plurality of teeth are positioned in between the offset planes and the cutting slope; and
 a plurality of teeth establishing a cutting point on a first end of the blade.

18. The surgical blade of claim 17 wherein the cutting point has a radius.

19. The surgical blade of claim 18 wherein the plurality of teeth positioned between the offset planes are positioned along a radius and have cutting tips extending towards the cutting point.

20. The surgical blade of claim 17 wherein the blade comprises a neck portion and a saw attachment base.

21. The surgical blade of claim 17 wherein the blade comprises a rectangular shape.

22. The surgical blade of claim 17 wherein the blade comprises a trapezoidal shape.

23. The surgical blade of claim 17 wherein the blade does not have teeth on four surfaces and accommodates the cutting slope on a fifth surface, and the cutting point on a sixth surface.

24. A method for performing a wedge-osteotomy comprising:
 providing a blade having a bottom plane extending between first and second ends, a plurality of teeth establishing a cutting point on the first end of the blade, and a cutting slope defining a second plane that intersects the bottom plane, the cutting slope comprising a plurality of offset planes positioned along the cutting slope wherein each of the plurality of offset planes has an upper surface that is parallel to the bottom plane and wherein teeth are positioned in between each of the offset planes and the cutting slope;
 attaching the blade to a surgical saw; and
 advancing the blade through a bone by oscillating the blade along a first plane parallel to the bottom plane to create a wedge osteotomy.

* * * * *